United States Patent
Denzel et al.

[11] 3,933,823
[45] Jan. 20, 1976

[54] ISOXAZOLOPYRIDINE KETONE DERIVATIVES

[75] Inventors: Theodor Denzel, Nurnberg; Hans Hoehn, Tegernheim, both of Germany

[73] Assignee: E. R. Squibb & Sons, Inc., Princeton, N.J.

[22] Filed: Mar. 5, 1973

[21] Appl. No.: 337,776

Related U.S. Application Data

[62] Division of Ser. No. 129,198, March 29, 1971, Pat. No. 3,736,327.

[52] U.S. Cl. ............... 260/268 BC; 260/250 R; 260/256.4 R; 260/293.58; 260/296 H
[51] Int. Cl.[2] .............................. C07D 295/12
[58] Field of Search ..... 260/293.58, 268 BC, 296 H

*Primary Examiner*—Donald G. Daus
*Assistant Examiner*—Jose Tovar
*Attorney, Agent, or Firm*—Lawrence S. Levinson; Merle J. Smith

[57] ABSTRACT

New isoxazolo[5,4-b]pyridine-5-ketones having the general formula

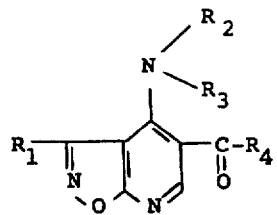

as well as their salts, are useful as central nervous system depressants. These compounds also increase the intracellular concentration of adenosine-3',5'-cyclic monophosphate.

5 Claims, No Drawings

ISOXAZOLOPYRIDINE KETONE DERIVATIVES

This application is a division of application Ser. No. 129,198, filed Mar. 29, 1971, U.S. Pat. No. 3,736,327, issued May 29, 1973.

SUMMARY OF THE INVENTION

This invention relates to new isoxazolo[5,4-b]pyridine-5-ketone derivatives and salts thereof. These new compounds have the general formula

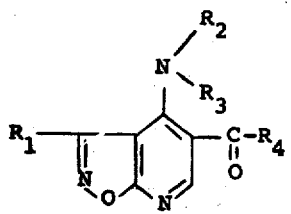

$R_1$ is hydrogen or lower alkyl. The basic nitrogen group

is an acyclic amino moiety wherein $R_2$ and $R_3$ each is hydrogen, lower alkyl, phenyl, substituted phenyl (i.e., the phenyl ring contains one or two simple substituents, e.g., a halogen, preferably chlorine, or trifluoromethyl), phenyl-lower alkylene or di-lower alkylamino-lower alkylene (preferably only one of these).

The basic nitrogen groups may also form a heterocycle of 3-,5- or 6-members in which an additional nitrogen is present, i.e., the aziridinyl, pyrrolidino, piperidino, pyrazolyl, pyrimidinyl, pyridazinyl or piperazinyl radicals, each of which may also bear as a substituent a hydroxy-lower alkyl group or one or two lower alkyl groups. $R_4$ is alkyl, cycloalkyl, phenyl or substituted phenyl. These radicals may also bear a hydroxy or a hydroxy-lower alkyl group.

DETAILED DESCRIPTION

The symbols have the following meanings in formula I and throughout this specification.

$R_1$ is hydrogen or lower alkyl. The basic nitrogen group

is an acyclic amino group wherein $R_2$ and $R_3$ each is hydrogen, lower alkyl, phenyl, substituted phenyl (i.e., the phenyl ring contains one or two simple substituents including halogen or trifluoromethyl), phenyl-lower alkylene or di-lower alkylamino-lower alkylene (preferably there is only one of these substituents). This basic group may also form a heterocycle of 3-,5- or 6-members in which an additional nitrogen is present, in particular, aziridinyl, pyrrolidino, piperidino, pyrazolyl, pyrimidinyl, pyridazinyl or piperazinyl radicals, each of which may also bear as a substituent a hydroxy-lower alkyl group or one or two lower alkyl groups. That is to say, $R_2$ and $R_3$ each is hydrogen, lower alkyl, $R_5$, $R_6$-phenyl (wherein $R_5$ and $R_6$ each is hydrogen, halogen or trifluoromethyl), phenyl-lower alkylene, or di-lower alkylamino-lower alkylene or $R_2$ and $R_3$ together with the nitrogen to which they are attached form one of the heterocyclics mentioned above or the $R_7$-mono-substituted or $R_7$, $R_8$-disubstituted derivative (wherein $R_7$ and $R_8$ are the substituents lower alkyl or hydroxy-lower alkyl in addition to hydrogen).

The lower alkyl and lower alkylene groups in any of the foregoing radicals are straight or branched chain hydrocarbon groups of up to eight carbon atoms like methyl, ethyl, propyl, isopropyl, butyl, t-butyl and the like. The lowest four members are preferred. Benzyl and phenethyl are the preferred phenyl-lower alkylene groups. All four halogens are included, but chlorine is preferred.

The products of the examples which are representative of the various compounds of this invention constitute preferred embodiments. Most preferably $R_3$ is hydrogen, particularly when $R_2$ includes a cyclic substituent or a substituted or unsubstituted acyclic group. Especially preferred compounds of formula I are those wherein $R_1$ is methyl, $R_2$ is butyl, phenyl, substituted phenyl and tertiary amine, $R_3$ is hydrogen and $R_4$ is methyl.

The new compounds of formula I are formed by the following series of reactions. The symbols in the structural formulas have the same meaning as previously described.

A 5-aminoisoxazole of the formula

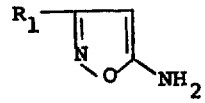

[produced by reacting 3-iminobutyronitrile with hydroxylamine analogous to the procedure described in Ann, Chem. 624,22(1959),] is made to react with an alkoxymethyleneaceto-acetic acid ester of the formula (III)   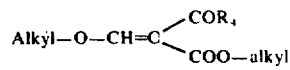

by heating at a temperature of about 120°-130°C. The resulting compound of the formula (IV)

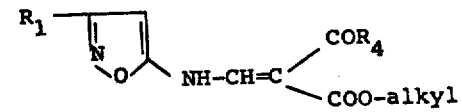

is cyclized in an inert organic solvent, such as diphenyl ether at about 230° to about 260°C. while distilling off the alcohol formed, producing a compound of the formula (V)

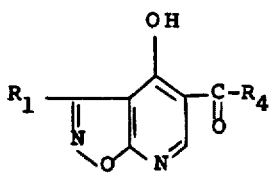

with a hydroxy group in the 4-position.

This 4-hydroxy compound is refluxed for several hours with a phosphorus halide like phosphorus oxychloride to obtain the intermediate of the formula (VI)

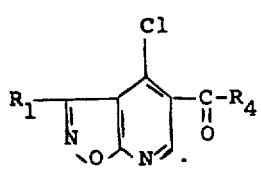

The product of formula I is then prepared from a compound of formula VI by reaction with the appropriate primary or secondary amine of the formula (VII)

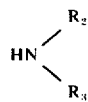

This reaction is effected by treating the reactants either at room or elevated temperature. For some cases it may be advantageous to make use of an autoclave.

The compounds of formula I form salts which are also part of this invention. The salts include acid-addition salts, particularly the non-toxic, physiologically acceptable members. The bases of formula I form salts by reaction with a variety of inorganic and organic acids providing acid addition salts including, for example, the hydrohalides (especially the hydrochloride and hydrobromide), sulfate, nitrate, phosphate, oxalate, tartrate, malate, citrate, picrate, acetate, ascorbate, succinate, arylsulfonates like benzenesulfonate and toluenesulfonate, alkanesulfonates like methanesulfonate, cyclohexanesulfonate, cyclohexanesulfamate, etc. The acid addition salts frequently provide a convenient means for isolating the product, e.g., by forming and precipitating the salt in an appropriate menstruum in which the salt is insoluble, then after separation of the salt, neutralizing with a base such as barium hydroxide or sodium hydroxide, to obtain the free base of formula I. Other salts may then be formed from the free base by reaction with an equivalent of acid.

The new compounds of this invention are central nervous system depressants and may be used as tranquilizers or ataractic agents for the relief of anxiety and tension states, for example, in mice, cats, rats, dogs and other mammalian species, in the same manner as chlordiazepoxide. For this purpose a compound or mixture of compounds of formula I, or non-toxic, physiologically acceptable acid addition salt thereof, may be administered orally or parenterally in a conventional dosage form such as tablet, capsule, injectable or the like. A single dose, or preferably 2 to 4 divided daily doses, provided on a basis of about 1 to 50 mg. per kilogram per day, preferably about 2 to 15 mg. per kilogram per day, is appropriate. These may be conventionally formulated in an oral or parenteral dosage form by compounding about 10 to 250 mg. per unit of dosage with conventional vehicle, excipient, binder, preservative, stabilizer, flavor or the like as called for by accepted pharmaceutical practice.

The new compounds also increase the intracellular concentration of adenosine-3', 5'-cyclic monophosphate, and thus by the administration of about 1 to 100 mg./kg./day, preferably about 10 to 50 mg./kg., in single or two to four divided doses in conventional oral or parenteral dosage forms such as those described above may be used to alleviate the symptoms of asthma.

The following examples are illustrative of the invention. All temperatures are on the centrigrade scale.

EXAMPLE 1

5-Acetyl-4-(n-butylamino)-3-methylisoxazolo[5,4-b]pyridine a. (3-Methyl-5-isoxazolyl)aminomethyleneacetoacetic acid ethyl ester 98 g. of 3-methyl-5-aminoisoxazole (1 mol.) and 186 g. of ethoxymethyleneacetoacetic acid ethyl ester (1 mol.) are heated with stirring for 45 minutes at 130°. After this period, ethanol is removed under reduced pressure. The residue solidifies on cooling and is recrystallized from ethanol, m.p. 93°–95°, yield 208 g. (87%).

b. 5-Acetyl-4-hydroxy-3-methylisoxazolo[5,4-b]pyridine 23.8 g. of (3-methyl-5-isoxazolyl)aminomethyleneacetoacetic acid ethyl ester (0.1 mol.) are quickly added to 100 ml. of vigorously refluxing diphenyl ether. After 5 minutes, the reaction mixture is cooled, as rapidly as possible. After addition of 100 ml. diethyl ether, 5-acetyl-4-hydroxy-3-methylisoxazolo[5,4-b]pyridine crystallizes and is filtered off. Recrystallization from methanol yields 9.5 g. (49.5%) of pure product, m.p. 162°.

c. 5-Acetyl-4-chloro-3-methylisoxazolo[5,4-b]pyridine 38.4 g. of 5-acetyl-4-hydroxy-3-methylisoxazolo[5,4-b]-pyridine (0.2 mol.) in 100 ml. of phosphorus oxychloride are heated for 5 hours at 80°. After this time, the excess phosphorus oxychloride is removed in vacuo and the residue is carefully neutralized with saturated sodium bicarbonate solution. The chloro compound is extracted three times with 100 ml. portions of chloroform. The organic layer is collected, dried over sodium sulfate and the solvent evaporated. The solid residue is recrystallized from petroleum ether. Yield, 33 g. (83%) of 5-acetyl-4-chloro-3-methylisoxazolo[5,4-b]pyridine, m.p. 63°.

d. 5-Acetyl-4-(n-butylamino)-3-methylisoxazolo[5,4-b]-pyridine 2.1 g. of 5-acetyl-4-chloro-3-methylisoxazolo[5,4-b]-pyridine (0.01 mol.) are added with stirring to 2.2 g. of n-butylamine (0.03 mol.). After 5 minutes the mixture is diluted with 50 ml. water and the 5-acetyl-4-(n-butylamino)-3-methylisoxazolo[5,4-b]pyridine which precipitates is filtered off and recrystallized from petroleum ether, yield 2.2 g. (90%), m.p. 116°–117°.

The hydrochloride salt is produced by treating the above product with dilute ethanolic hydrogen chloride solution.

By utilizing sec.-butylamine in the procedure of part d, 5-acetyl-4-(sec.-butylamino-3-methylisoxazolo[5,4-b]pyridine is obtained, m.p. 79°–81°.

The following additional products are produced by substituting the appropriately substituted starting material for the 3-methyl-5-aminoisoxazole or ethoxymethyleneacetoacetic acid ethyl ester in part a or butylamine in part d of Example 1, respectively:

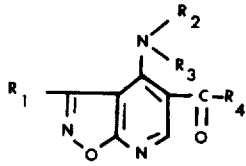

| Example | $R_1$ | $R_4$ | $N{<}^{R_2}_{R_3}$ |
|---|---|---|---|
| 2 | H | $C_2H_5$ | $-NH_2$ |
| 3 | $C_2H_5$ | $C_2H_5$ | $-N(C_2H_5)_2$ |
| 4 | $CH_3$ | $C_3H_7$ | $-N(CH_3)_2$ |
| 5 | H | $C_4H_9$ | $-NHC_4H_9$ |
| 6 | $CH_3$ | cyclobutyl | $-NHC_4H_9$ |
| 7 | $CH_3$ | cyclopentyl | $-N(C_5H_{11})_2$ |
| 8 | $CH_3$ | cyclohexyl | $-NH-C_6H_5$ |
| 9 | $CH_3$ | $CH_3$ | -N⊲ (aziridinyl) |
| 10 | H | $C_2H_5$ | -N (pyrrolidinyl) |
| 11 | $CH_3$ | $CH_3$ | -N (piperidinyl) |
| 12 | $CH_3$ | $CH_3$ | -N⌒N (piperazinyl) |
| 13 | $CH_3$ | $CH_3$ | -N⌒N (morpholinyl) |
| 14 | $CH_3$ | $CH_3$ | -N⌒NC_2H_4OH |
| 15 | $CH_3$ | -C_6H_5 | $-NH_2$ |
| 16 | $CH_3$ | -C_6H_4-CH_3 | $-NHC_4H_9$ |
| 17 | H | -C_6H_4-Cl | $-NHCH_3$ |
| 18 | $C_2H_5$ | -C_6H_4-OH | $-NH-C_6H_3Cl_2$ |
| 19 | $C_2H_5$ | cyclohexyl-OH | $-NHCH_3$ |
| 20 | $C_2H_5$ | -C_6H_5 | $-NH-C_6H_4-CF_3$ |
| 21 | $C_2H_5$ | $C_2H_5$ | $-N(H)-C_2H_4N(C_2H_5)_2$ |
| 22 | H | $CH_3$ | $-NHCH_2CH_2-C_6H_5$ |

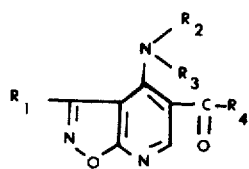

| Example | $R_1$ | $R_4$ | $N{<}^{R_2}_{R_3}$ |
|---|---|---|---|
| 23 | H | $CH_3$ | 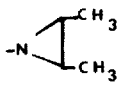 |
| 24 | H | $CH_3$ | 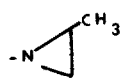 |

What is claimed is:

1. A compound of the formula

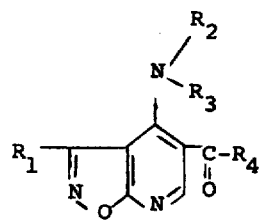

wherein $R_1$ is hydrogen or lower alkyl;

is $R_7$-piperidino or $R_7$-piperazinyl; $R_4$ is lower alkyl, cyclo-lower alkyl or phenyl; and $R_7$ is hydrogen, lower alkyl or hydroxy-lower alkyl, and physiologically acceptable acid addition salts thereof.

2. A compound as in claim 1 wherein $R_1$ and $R_4$ each is lower alkyl.

3. A compound as in claim 1 wherein $R_1$ and $R_4$ each is methyl and

is piperidino.

4. A compound as in claim 1 wherein $R_1$ and $R_4$ each is methyl and $-N{<}^{R_2}_{R_3}$ is piperazino.

5. A compound as in claim 1 wherein $R_1$ and $R_4$ each is methyl and

is (hydroxyethyl)piperazino.

* * * * *